United States Patent [19]

Gikas

[11] 4,253,767
[45] Mar. 3, 1981

[54] PHOTO-INTEGRATED DENSITOMETER

[75] Inventor: Giorgos X. Gikas, Washington, D.C.

[73] Assignee: The Gillette Company, Boston, Mass.

[21] Appl. No.: 105,459

[22] Filed: Dec. 20, 1979

[51] Int. Cl.³ .............................................. G01N 21/84
[52] U.S. Cl. ..................................... 356/426; 356/432
[58] Field of Search ............... 356/426, 432, 434, 440, 356/446

[56] References Cited

U.S. PATENT DOCUMENTS 3,736,064   5/1973   Kent et al. ........................... 356/425

FOREIGN PATENT DOCUMENTS 634093   11/1978   U.S.S.R. .................................. 356/432

Primary Examiner—R. A. Rosenberger
Attorney, Agent, or Firm—Richard A. Wise; Raymond J. De Vellis

[57] ABSTRACT

A photo-integrated densitometer is arranged to evaluate the relative oiliness and stringiness of hair tresses under dynamic conditions.

8 Claims, 3 Drawing Figures

PHOTO-INTEGRATED DENSITOMETER

BACKGROUND OF THE INVENTION

1. Field of the Invention

This invention relates to apparatus for indicating oiliness and stringiness of hair tresses and, more particularly, to apparatus for providing a relative indication of oiliness and stringiness of hair tresses under dynamic conditions.

2. Description of the Prior Art

One of the negative aspects of some hair conditioners and creme rinses is that they can make hair look "oily" or "stringy". There are times when women want their hair to be shiny, silky, or lustrous. Moreover, in conditioning shampoos, the amount and nature of the conditioner added to the shampoo is very critical and optimization is not an easy task. For this reason, several attempts have been made to determine the effect of various conditioners on hair tresses. For example, hair luster has been studied by measuring light reflected from hair tresses using a reflectometer. A change in luster after a hair tress has been treated by a creme rinse is measured by use of a Hunter-lab D40 Reflectometer in a mode normally used for measuring whiteness. In addition, investigators have examined many other ways for determining the amount of soil deposited on hair and the efficiency of various detergents for removing soil from the hair.

The aforementioned methods and apparatus are limited in accuracy and applicability. For example, the sensitivity of the reflectometer is quite low when blond hair is not used, and the hair tress is usually in a static position in a horizontal plane and not in a randomized and moving configuration. It has been determined that oiliness and stringiness of hair tresses are better tested under dynamic conditions that are closer to reality than measurements made on individual fibers.

Accordingly, it is desirable to arrange an instrument to accurately evaluate the relative oiliness and stringiness of hair tresses under dynamic conditions.

SUMMARY OF THE INVENTION

An apparatus for indicating degree of adhesion between hair fibers of a hair tress comprises a light source for transmitting a light beam, light detecting means providing an electrical signal proportional to intensity of incident light from the light source transmitted through said hair tress, and holding means rotatably driven by a motor. Circuit means electrically connected to the light detecting means integrates the electrical signal over one revolution of the holding means.

DESCRIPTION OF THE PREFERRED EMBODIMENT

Figure 1:
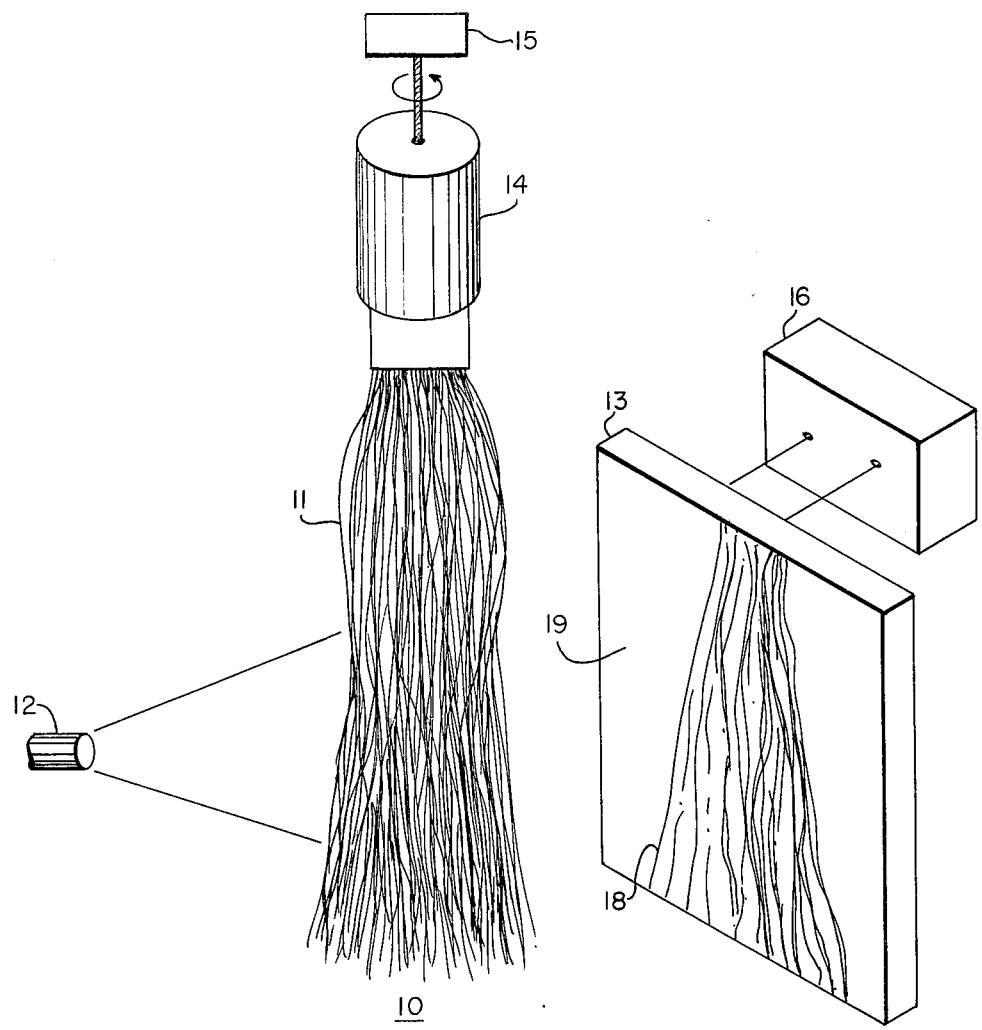
FIG. 1 is a block diagram of a photo-integrated densitometer arranged according to the invention.

It has been determined that hair fibers tend to adhere to each other when a hair tress is coated by a conditioner. The maximum adhesion, and therefore, stringiness, occurs when all the hair fibers adhere to each other. The photo-integrated densitometer 10 shown in the block diagram of FIG. 1 and further described below, is arranged, according to the invention, to provide a measurement of the degree or tendency of hair fibers to adhere to each other by measuring the intensity of light transmitted through a rotating hair tress 11 placed between a light source 12 and a photocell 13. The hair tress 11 is vertically suspended from a holder 14 in a plane substantially orthogonal to a plane surface containing the light source 12 and photocell 13. The tress 11 is rotated by a motor 15 slowly around its longitudinal axis at substantially 1 rpm to expose substantially all outward surfaces of the tress 11 to radiation from the light source 12. The photocell 13 is adapted to generate an electrical output signal proportional to the intensity of incident radiation or the light from the source 12 transmitted through the rotating hair tress 11. The photocell electrical output signal is integrated over the 360° revolution of the hair tress 11 and then recorded by a suitable electric circuit 16. The amplitude of the integrated electrical signal is indicative of the tendency of the hair fibers of all surfaces of the hair tress exposed to the radiation to adhere to each other. It has been determined that the amplitude of the integrated electrical signal increases in proportion to the increased tendency of hair fibers to adhere to each other. Thus, a measurement by the densitometer 10 of the stringiness of a hair tress coated by a conditioner may be compared with measurements made by the densitometer 10 on other tresses purposely coated by various solutions selected to cause differing numbers of the hair fibers to adhere to each other to provide a relative measurement of stringiness of the conditioned hair tress.

Figure 2:
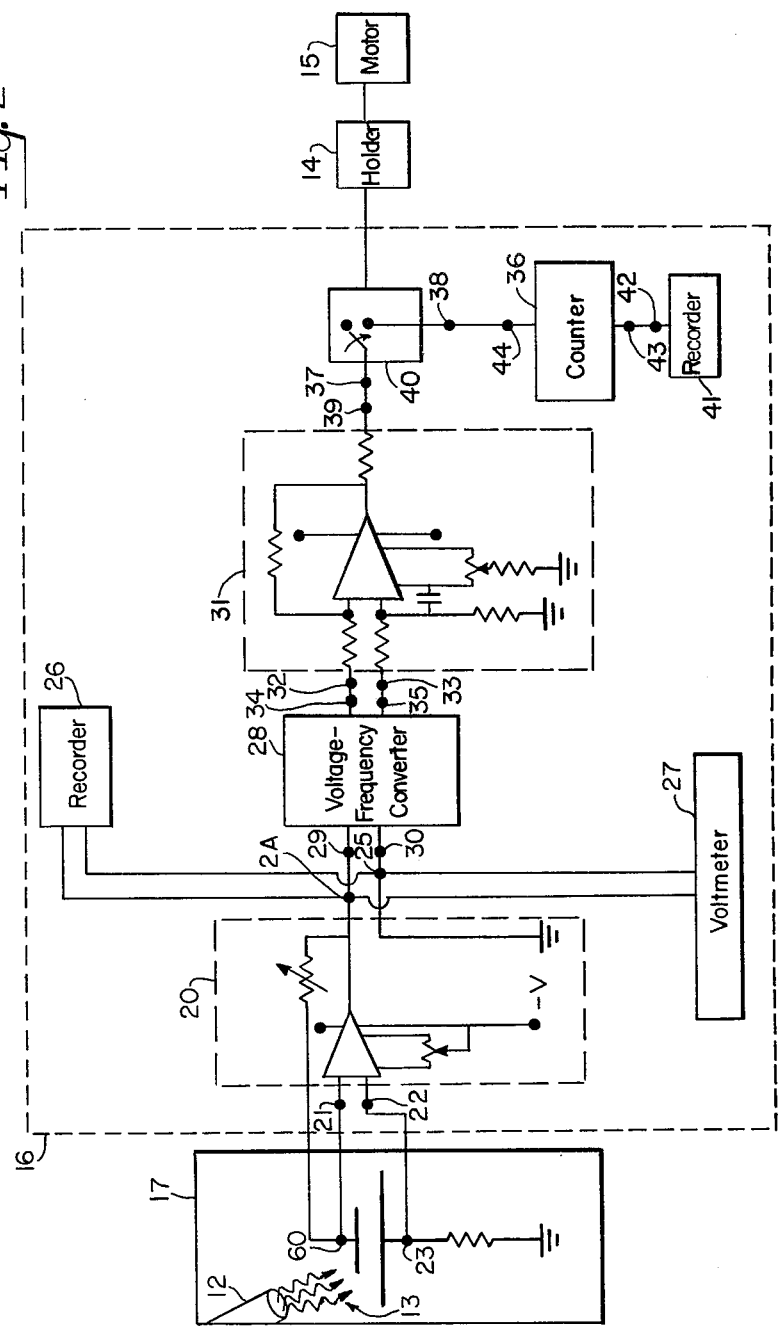
FIG. 2 is a more detailed schematic diagram of the photo-integrated densitometer shown in FIG. 1.

Referring to FIG. 2 there is shown a more detailed schematic diagram of the photo-integrated densitometer 10 including the light source 12 and the photocell 13 enclosed in a substantially light-proof housing 17 adapted to substantially prevent erroneous indications caused by light from another source. The housing 17 has an interior painted a matte black to minimize light reflected toward the photocell 13 from interior housing walls. An example of the light source 12 is a fiber light source such as the Ealing 22-0004 available from Ealing, Cambridge, Mass. The light transmitted by the light source 12 is directed toward the hair tress 11 vertically suspended from the holder 12 and disposed within the housing 17. A portion of the light is reflected by the tress 11 while the remaining light source passes through the tress 11 to present a shadow 18 on an exposed surface area 19 of the photocell 13, as shown in FIG. 1. The photocell 13 may be a solid-state photosensitive electron device adapted to provide an electrical output signal proportional to the intensity of the radiation incident on the exposed surface area 19. An example of a suitable photocell 13 is a DP-5 International Rectifier photocell available from International Rectifier, El Segundo, Calif.

The photocell 13 is electrically connected to electric circuit means 16 adapted to integrate the photocell output signal over one complete revolution of the hair tress 11. The electric circuit means 16 include a photovoltaic current amplifier 20 having a first input terminal 21 connected to a negative terminal 60 of the photocell 13 and a second input terminal 22 connected to a positive terminal 23 of the photocell 13. The amplifier 20 is arranged, as known in the art, to provide an output signal at amplifier output terminals 24,25 that is proportional to the magnitude of the output signal from the photocell 13. An example of the amplifier 20 is current amplifier model 741, available from Fairchild Industries, Mountainview, Calif.

A chart recorder or oscilloscope 26 and a digital voltmeter 27 are electrically connected in parallel across the output terminals 24,25 of the amplifier 20. The chart recorder or oscilloscope 26 is calibrated to provide a visual indication or graphical representation of the amplitude of the output signal from the amplifier 20 over a predetermined time period. The digital voltmeter 27 provides a means for calibrating the densitometer 10 by indicating a predetermined voltage indicative of an amplifier output signal that would be supplied under certain test conditions. For example, when the tress 11 is removed from the closed housing 17 and the photocell 13 is turned off, the digital voltmeter 27 is adjusted to record a null. The photocell 13 is then turned on, and the gain of the amplifier 20 is adjusted until the digital voltmeter records a convenient voltage level proportional to the total light flux emitted by the light source 12.

The amplifier output signal is also coupled to a voltage-frequency converter module 28 having input terminals 29,30 respectively connected to the amplifier output terminals 24,25. The converter module 28 is adapted to convert the analog voltage signal from the amplifier 20 to a digital signal. An example of a suitable voltage-frequency converter module is Action Pak Model 7500 Integrator/Totalizer available from Action Instruments Co. Inc., San Diego, Calif.

The digital output signal from the voltage-frequency converter module 28 is coupled to a differential amplifier 31 having input terminals 32,33 respectively connected to the output terminals 34,35 of the converter module 28. The differential amplifier 31 is arranged, as known in the art, to provide an output signal proportional to the algebraic difference between the signals present at its input terminals 32,33. An example of the differential amplifier 31 is IG Type 301 available from National Semiconductor, Santa Clara, Calif.

The output signal from the differential amplifier 31 is coupled to an integrator-counter circuit 36 via a microswitch 40. The integrator-counter circuit 36 is arranged, as known in the art, to integrate the output signal from the differential amplifier 31 over one complete revolution of the hair tress 11. An integrated output signal from circuit 36 is coupled to a suitable recorder 41 having an input terminal 42 connected to an output terminal 43 of circuit 36. The amplitude of the integrated output signal from circuit 36 is indicative of the tendency of the hair fibers of the hair tress 11 to adhere to each other.

The microswitch 40 is mechanically coupled to the motor driven holder 14 with terminals 37,38 respectively connected to an output terminal 39 of the amplifier 31 and an input terminal 44 of the integrator-counter circuit 36. The microswitch 40 is arranged, as known in the art, to operate in response to movement of the holder 14 to provide a conductive path between the amplifier 31 and integrator-counter 36 only during one full revolution of the hair tress 11, whereby the output signal from amplifier 31 is integrated by circuit 36 over one complete revolution of the hair tress.

Figure 3:
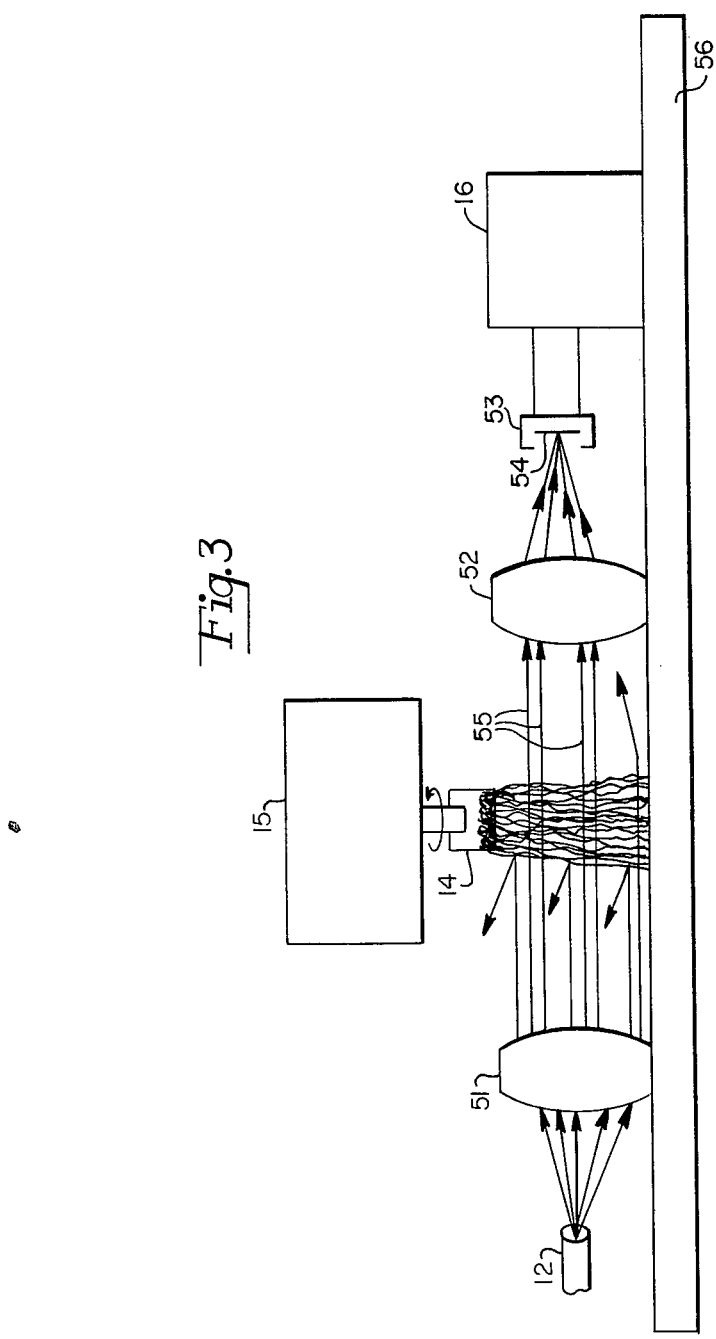
FIG. 3 is a schematic drawing of another embodiment of the invention.

Referring to FIG. 3, there is shown a schematic drawing of another embodiment of the invention including the light source 12, first 51, and second 52 Fresnel lenses, and a photocell 53 having a relatively small surface area 54 for receiving incident radiation. An example of photocell 53 is model Hav-4000A available from EG&G, Salem, Mass. The first Fresnel lens 51 is interposed between the light source 12 and the second Fresnel lens 52. The first Fresnel lens 51 is arranged to collimate the radiation from the light source 12. The second Fresnel lens 52 is interposed between the first Fresnel lens 51 and the photocell 53. The second Fresnel lens 52 is arranged to focus the nearly parallel light rays 55 transmitted from the first lens 51 through the hair tress 11 to a point beam incident on the photocell surface 54. The photocell 53 is electrically connected to the electric circuit means 16 described above in reference to FIG. 2.

Under test conditions, the hair tress 11 may be vertically suspended from the motor driven holder 14 between the first 51 and second 52 Fresnel lenses and slowly rotated by the motor 15 about its vertical axis at substantially 1 rpm to expose substantially all surfaces of the tress to radiation from the light source 12. The photocell 53 acts in response to the incident radiation to provide an electrical output signal proportional to the intensity of the focused beam. The electric circuit means 16 integrates the electrical output signal from the photocell 53 over one complete revolution of the hair tress and supplies an output signal to a recorder 41 that is indicative of the tendency of the hair fibers to adhere to each other. Alternatively, the same test may be performed on a hair tress in vivo by rotating a platform 56 supporting the light source 12, lenses 51,52, photocell 53, and electric circuit means 16 while a hair tress from the head of an individual is inserted between the lenses 51,52.

A preferred embodiment of the invention has been shown and described. Various other embodiments and modifications thereof will be apparent to those skilled in the art, and will fall within the scope of the invention as defined in the following claims.

What is claimed is:

1. Apparatus for indicating degree of adhesion between hair fibers of a hair tress comprising:
    a light source for transmitting a light beam;
    light detecting means providing an electrical signal proportional to intensity of incident light from said light source transmitted through said hair tress;
    holding means rotatably driven by a motor to provide an angular displacement of said hair tress relative to said light source; and
    circuit means electrically connected to said light detecting means for integrating said electrical signal over one revolution of said holding means.

2. Apparatus according to claim 1, wherein said holding means is adapted to suspend said hair tress so that said light beam is transmitted through said hair tress to said light detecting means.

3. Apparatus according to claim 1, wherein said holding means is adapted to hold and rotate said light source and said light detecting means around said hair tress interposed between said light source and light detecting means so that said light beam is transmitted through said hair tress to said light detecting means.

4. Apparatus according to claim 1, further including a substantially light proof housing containing said light source and said light detecting means.

5. Apparatus according to claim 1, further including recording means electrically connected to said circuit means for recording said integrated electrical signal.

6. Apparatus for indicating degree of adhesion between hair fibers of a hair tress comprising:

a light source for transmitting light;

light detecting means providing an electrical signal proportional to the intensity of incident light transmitted from said light source through a hair tress;

holding means for providing an angular displacement of said hair tress relative to said light source to expose substantially all outward surfaces of said tress to radiation from said light source;

circuit means electrically connected to said light detecting means for integrating said electrical signal over a 360° angular displacement of said hair tress relative to said light source; and means for recording said integrated electrical signal.

7. Apparatus according to claim 6, further including a substantially light proof housing containing said light source and said light detecting means.

8. Apparatus according to claim 6, further including first and second lenses interposed between said light source and said light detecting means, said first lens being adapted to collimate said light transmitted from said light source and said second lens being adapted to focus said light transmitted through said hair tress to a point beam incident on said light detecting means.

* * * * *